United States Patent [19]

Zaiger et al.

[11] Patent Number: Plant 7,420

[45] Date of Patent: Jan. 15, 1991

[54] INTERSPECIFIC TREE "FLAVOR QUEEN"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 427,863

[22] Filed: Oct. 27, 1989

[51] Int. Cl.[5] ..... A01H 5/00

[52] U.S. Cl. ..... Plt./38

[58] Field of Search ..... Plt./38, 39

*Primary Examiner*—Howard J. Locker

[57] ABSTRACT

A new and distinctive interspecific tree (Plum×Plum Cot); its novelty consists of the following unique combination of desirable features.

1. The ability to be a regular and productive bearer of large size fruit.
2. Fruit with excellent flavor and eating quality.
3. Fruit having a high degree of soluble solids (average 18.1 Brix).
4. Vigorous semi-spreading growth.
5. The ability of the fruit to stay firm on the tree 12–15 days after maturity (shipping ripe).
6. Uniform ripening of the fruit throughout the tree.

1 Drawing Sheet

ORIGIN OF THE VARIETY

The present new and distinct variety of interspecific tree (Plum×Plum Cot) was originated by us in the experimental orchard located near Modesto, Calif. as a first generation seedling from a cross between Mariposa Plum (non-patented) and a selected seedling with the identification number 4G1180. The pollen parent 4G1180 (Plum Cot) originated from a seedling of open pollinated seed of Red Beaut Plum (U.S. Plant Pat. No. 2,539) which had crossed with an apricot of unknown parentage.

ASEXUAL REPRODUCTION OF THE VARIETY

The present variety of interspecific tree was asexually reproduced by budding, as performed by us in the experimental orchard located at Modesto, Calif. and shows that said characteristics of the tree and its fruit come true to form and are established and transmitted through succeeding propagations.

SUMMARY OF THE VARIETY

A new and distinct variety of interspecific tree (Plum×Plum Cot) which is of large size, vigorous, medium dense, semi-spreading growth and a regular and productive bearer of large, yellow flesh clingstone fruit. The present variety of interspecific tree is further characterized as to its novelty by producing fruit that will hold firm on the tree 12 to 15 days after maturity (shipping ripe), having firm flesh texture which is more characteristic of plum than apricot, being excellent in flavor and eating quality and having higher soluble solids (Average 18.1 Brix) than most commercial plums.

DESCRIPTION OF THE PHOTOGRAPHS

The accompanying color photographs show typical specimens of the fruit and foliage of the new interspecific variety, with the exterior and cross sectional view of the fruit divided in the suture plane to reveal flesh coloration, pit cavity and showing a stone remaining in place. The photographs were taken shortly after being picked (firm ripe) and the colors are as nearly true as is reasonably possible in a color representation of this type.

DESCRIPTION OF THE VARIETY

The following is a detailed botanical description of the new interspecific tree, its fruit and foliage as based on observations of specimens grown near Modesto, Calif., with color terminology (except those in common terms) in accordance with Reinhold Color Atlas by A. Kornerup and J. H. Wanscher.

Tree:

*Size.*—Large.
*Vigor.*—Vigorous.
*Form.*—Semi-spreading.
*Density.*—Medium dense.
*Shape.*—Usually pruned to vase shape.

*Bearer.*—Regular.
*Production.*—Productive.

Trunk:
*Size.*—Medium to large.
*Surface.*—Shaggy.
*Color.*—Brown to grayish brown (6-D-4) to (6-E-3).

Branches:
*Size.*—Medium to large.
*Surface.*—Medium rough.
*Lenticels.*—Few in number. Small size.
*Color.*—New growth — green to reddish brown. Mature growth — brown to grayish brown.

Leaves:
*Size.*—Medium to large. Average width — 1½" to 1¾". Average length — 4¼" to 5".
*Texture.*—Smooth.
*Petiole.*—Average length — ¾".
*Form.*—Oblanceolate. Pointed.
*Margin.*—Serrulate.
*Glands.*—Globose. Size — small to medium. Number varies from 1 to 3. Average number 2.
*Color.*—Upper surface — green to deep green (28-F-6) to (28-F-8). Lower surface — dull green to green (28-E-5) to (28-E-7).

Flower buds:
*Size.*—Medium.
*Length.*—Medium.
*Form.*—Plump, free.

Flowers:
*Size.*—Medium.
*Color.*—White to pale pink.
*Blooming period.*—Date of first bloom Mar. 1, 1987. Date of full bloom Mar. 6, 1987. Varies slightly with climatic conditions.

Fruit:
*Maturity when described.*—Firm ripe.
*Date of first picking.*—July 20, 1987.
*Date of last picking.*—July 28, 1987.
*Size.*—Medium to large — 2¼" to 2⅜". Average diameter axially 2" to 2⅛".
*Form.*—Nearly globose. Flattened at stem and apex.
*Suture.*—Shallow — most fruit round with some fruit being flat to very slightly lipped.
*Base.*—Retuse.
*Apex.*—Retuse.
*Cavity.*—Rounded to slightly elongated in suture plane. Average depth — ⅜". Average breadth — ⅜".

Flesh:
*Texture.*—Firm.
*Fibers.*—Few-tender.
*Ripens.*—Evenly.
*Flavor.*—Excellent, sweet, mild, subacid.
*Juice.*—Moderate.
*Aroma.*—Slight.
*Eating quality.*—Excellent.
*Color.*—Yellow to grayish yellow. (3-B-8) to (4-B-7).

Skin:
*Thickness.*—Thin to medium.
*Texture.*—Medium. Tenacious to flesh.
*Tendency to crack.*—None.
*Down.*—Wanting.
*Color.*—Olive yellow to yellow — (2-B-8) to (3-C-8).

Stone:
*Type.*—Clingstone.
*Size.*—Medium. Average length — 1". Average width — ¾". Average breadth — ½".
*Form.*—Ovid.
*Sides.*—Mostly equal — some unequal.
*Ridges.*—Sharp ridges extending across the surface of the stone on both sides of suture plane.
*Surface.*—Slightly pitted throughout.
*Apex.*—Cuspidate.
*Base.*—Rounded to straight.
*Tendency to split.*—None.
*Color.*—Varies from brown to golden brown (5-D-5) to (5-D-7).

Use: Dessert.
*Market.*—Local and long distance.

Keeping quality: Good.

Shipping quality: Fair to good.

The interspecific tree, its foliage, flowers and fruit herein described may vary in slight detail due to climatic, soil and environmental conditions under which the variety may be grown; the present botanical description being of the variety grown at Modesto, Calif.

We claim:

1. A new and distinct variety of interspecific tree, as illustrated and described, characterized by its large size, vigorous, semi-spreading growth and a productive and regular bearer of large, firm, yellow flesh, clingstone fruit; the fruit is further characterized by staying firm on the tree 12 to 15 days after maturity, having excellent flavor and eating quality with a high degree of soluble solids (average 18.1 Brix) and having good storage quality.

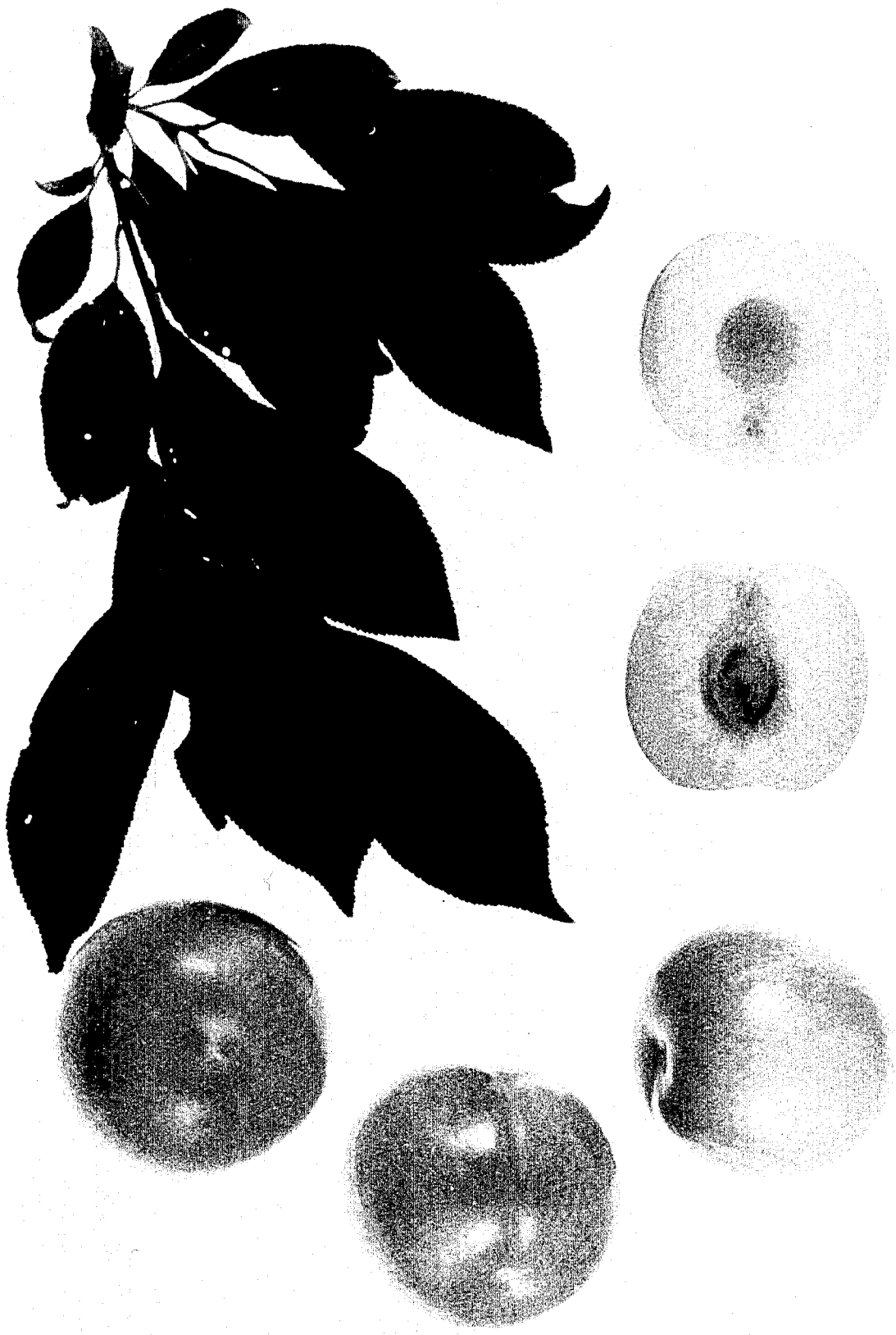

* * * * *